US00PP14461P29

(12) United States Plant Patent
Uchneat

(10) Patent No.: US PP14,461 P2
(45) Date of Patent: Jan. 13, 2004

(54) IMPATIENS PLANT NAMED 'BALPIXRECO'

(50) Latin Name: *Impatiens walleriana*
Varietal Denomination: Balpixreco

(75) Inventor: Michael S. Uchneat, St. Charles, IL (US)

(73) Assignee: Ball Floraplant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/107,847

(22) Filed: Mar. 26, 2002

(51) Int. Cl.[7] ..... A01H 5/00
(52) U.S. Cl. ..... Plt./317
(58) Field of Search ..... Plt./317

*Primary Examiner*—Anne Marie Grunberg
(74) *Attorney, Agent, or Firm*—Wood, Phillips, Katz, Clark & Mortimer

(57) ABSTRACT

A new and distinct Impatiens plant named 'Balpixreco', characterized by its small red and white bicolor flowers, compact growth habit and dark green leaves.

1 Drawing Sheet

Latin name of genus and species of plant claimed: *Impatiens walleriana.*
Variety denomination: 'Balpixreco'.

BACKGROUND OF THE INVENTION

The present invention comprises a new and distinct Impatiens plant, botanically known as *Impatiens walleriana* and hereinafter referred to by the cultivar name 'Balpixreco'.

'Balpixreco' is a product of a planned breeding program with the objective of developing Impatiens cultivars with small flowers and compact growth habits.

The female or seed parent of 'Balpixreco', 'Red Chico' (unpatented), has more compact growth habit than 'Balpixreco'. The male or pollen parent of 'Balpixreco', proprietary Impatiens variety designated SD01033-2 (unpatented), has pink and white bicolor flowers. The new cultivar was discovered and selected as a single flowering plant within the progeny of the above stated cross during October 1999 in a controlled environment at Elburn, Ill. The new cultivar was initially designated BFP-522.

Asexual reproduction of the new cultivar has been carried out at West Chicago, Ill. by terminal tip cuttings and has demonstrated that the unique characteristics of the new cultivar as herein described are firmly fixed and retained through successive generations of such asexual propagation.

SUMMARY OF THE INVENTION

It was found that the cultivar of the present invention:

(a) exhibits small red and white bi-color flowers;

(b) forms dark green foliage;

(c) exhibits a good basal branching character; and (d) exhibits a compact growth habit.

The new cultivar of the present invention can be compared to 'Fify Red' (U.S. Plant Pat. No. 11,753). However, in side-by-side comparisons, plants of the new cultivar are more vigorous have a shorter spur and different flower color than 'Fify Red'.

BRIEF DESCRIPTION OF PHOTOGRAPH

The accompanying photograph shows as nearly true as it is reasonably possible to make the same in color illustrations of this type, typical flower and foliage characteristics of the new cultivar. The plants were grown for 12 weeks in a greenhouse at West Chicago, Ill.

DETAILED BOTANICAL DESCRIPTION

The cultivar 'Balpixreco' has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Feb. 12, 2002. The readings were taken between 2:00 and 3:00 p.m. under natural daylight conditions.

Plants used for the following descriptions and measurements were grown in 10 cm pots for 12 weeks from rooted cuttings. The plants were produced from cuttings taken from stock plants and grown in a double polycarbonate covered greenhouse under conditions comparable to those used in commercial practice. A soilless growth medium was utilized while temperatures of approximately 68° to 75° F. (20° to 24° C.) during the day and approximately 55° to 65° F. (13° to 18° C.) during the night and light levels of 4,000 to 6,000 footcandles were maintained.

Classification:
*Botanical.*—*Impatiens walleriana*, cultivar'Balpixreco'.
Parentage:
*Female parent.*—Impatiens variety 'Red Chico'.
*Male parent.*—Proprietary Impatiens variety designated SD01033-2.
Propagation:
*Type cutting.*—Terminal tip.
*Time to initiate roots.*—Approximately 7 to 10 days.
*Time to develop roots.*—Approximately 21 to 30 days.
*Root descriptions.*—Fibrous, branching.

Plant description:

*Crop time.*—Approximately 4 to 6 weeks are required to produce a finished plant from rooted cuttings.

*Habit of growth.*—Compact with good basal branching. Pinching is not required.

*Form.*—Upright and mounded.

*Height of foliage.*—A mature plant, 12 weeks after the planting of a rooted cutting, commonly measures approximately 16.3 cm.

*Plant spread.*—Approximately 26 cm.

*Lateral branches.*—An average of 13 branches per plant, approximately 7 cm in length and 5 mm in diameter, glabrous and 146B in color. Internode length at the middle of the branch is approximately 1.7 cm.

*Foliage.*—Arrangement is alternate. Leaves are single, ovate with crenate, ciliate margin, acuminate apex, attenuate base and are at an acute angle to the stem. Upper and lower surfaces are glabrous. Leaf length is approximately 3 cm and width is approximately 2.1 cm. The upper surface of mature foliage is 139A and the lower surface is closest to 139A with splotches of 183D. Both upper and lower surfaces have pinnate venation. Venation of upper surface is 139D and the venation of the lower surface is 146B. The petiole length is approximately 19 cm, the diameter is approximately 2 mm and the color is lighter than 139D.

Flowering description:

*Flowering habit.*—Freely flowering.

*Natural flowering season.*—Year round in greenhouse environment and from spring through fall in outdoor garden.

Flower description:

*Type.*—Single and persistent.

*Size.*—Diameter is approximately 2.1 cm.

*Aspect.*—Flat.

*Corolla.*—Five petals with entire undulate margin, attenuate base and smooth texture. All petals have emarginate apex. Upper petal length is approximately 8 mm and width at widest point is 7 mm. Lower and lateral petal length is approximately 1 cm and width is approximately 6 mm. Petals vary in color. Some of the upper petals are entirely 155D, some are entirely 47A and others are 47A with small area of 155D at apex or along margin. Some of the lateral and lower petals are entirely 155D, some are entirely 47C and others are 47C with small area of 155D at apex or along margin. Color of lower surface of all petals is 46C at margin and middle and 47D at base.

*Peduncle.*—Glabrous, at an acute angle to the stem, approximately 1.7 cm in length and 1 mm in diameter. Peduncle color is 146B.

*Flower bud.*—Oval, approximately 8 mm in length and 5 mm in diameter at first color. Bud color is 39A.

*Sepals.*—Three. Lateral sepals are approximately 2 mm in length and 1 mm in width with acuminate apex and color of 146B. Lower sepal is modified into a spur.

*Spur.*—Sharply curved, 1.8 cm in length and gradually fades from 53A at distil end to 51C at proximal end.

*Reproductive organs.*—Five stamens, 3 mm in length. Anthers are fused around pistil, and 86A in color. Pollen has not been observed. Pistil length is 3 mm. Style length is <1 mm and color is 78A. Stigma length is <1 mm and color is 78A. Ovary is 2 mm in length and color is l43A.

Seed production: Seed production has not been observed.

Disease resistance: Resistance to pathogens has not been observed.

Hardiness zone: 'Balpixreco' is hardy in zones nine (9) and above.

I claim:

1. A new and distinct cultivar of Impatiens plant named 'Balpixreco' substantially as herein shown and described, which:

(a) exhibits small red and white bicolor flowers;

(b) dark green foliage;

(c) a compact growth habit; and (d) a good basal branching character.

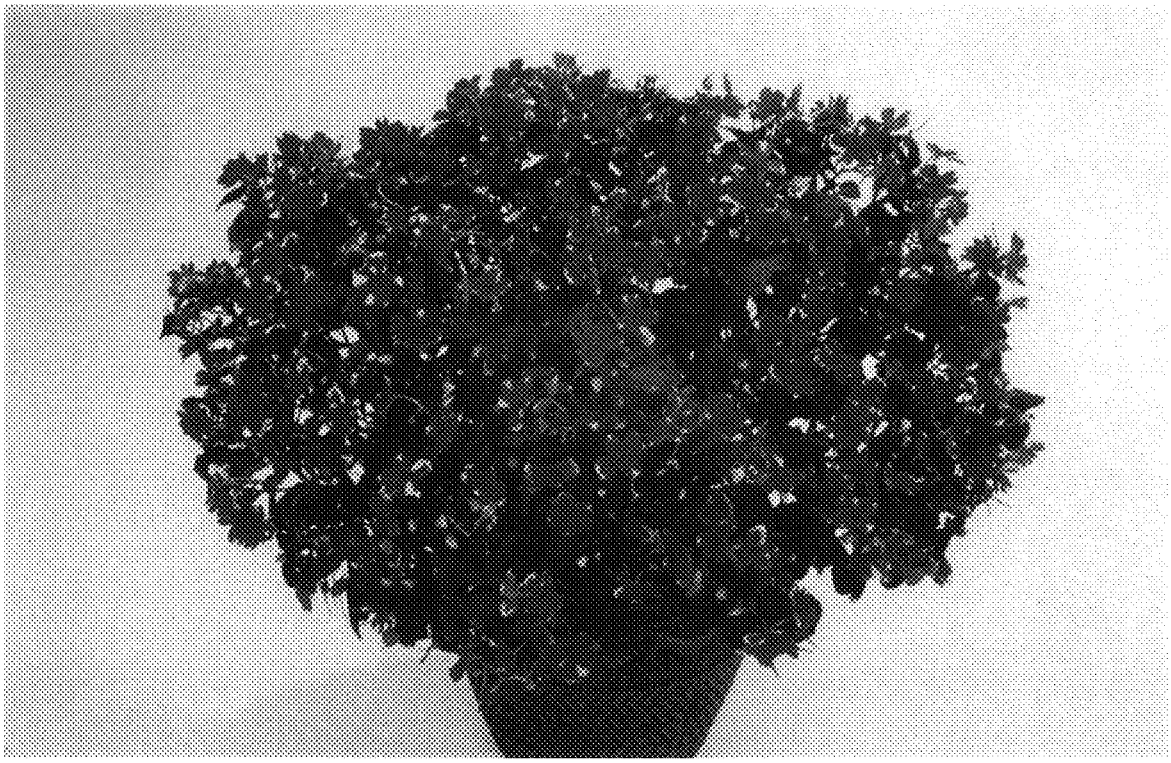

* * * * *